United States Patent [19]
Radwan et al.

[11] Patent Number: 5,688,509
[45] Date of Patent: Nov. 18, 1997

[54] CONTROLLED-RELEASE INSECT REPELLENT DEVICE

[75] Inventors: M. Nabil Radwan, Medina, Ohio; Gaylord Powers Allin, West Monroe, La.

[73] Assignee: Tenneco Packaging, Evanston, Ill.

[21] Appl. No.: 603,727

[22] Filed: Feb. 20, 1996

[51] Int. Cl.$^6$ .......................... A01N 65/00; A01N 25/00; A01N 37/02; A01N 37/00
[52] U.S. Cl. .............. 424/195.1; 424/405; 424/DIG. 10; 514/552; 514/557; 514/558; 514/919
[58] Field of Search ................. 424/195.1, DIG. 10, 424/405; 514/552, 557, 558, 919

[56] References Cited

U.S. PATENT DOCUMENTS

| | | | |
|---|---|---|---|
| 131,242 | 9/1872 | Baquol | 424/195.1 |
| 173,945 | 1/1876 | Hall et al. | 424/196.1 |
| 174,484 | 1/1876 | Cobb | 190/106 |
| 663,684 | 12/1900 | Rudisch | 424/416 |
| 3,882,226 | 5/1975 | Bradburne | 424/19 |
| 4,320,112 | 3/1982 | Jones et al. | 424/19 |
| 4,671,960 | 6/1987 | Thielen et al. | 424/195.1 |
| 4,891,222 | 1/1990 | Eichhoefer | 414/196.1 |
| 4,927,635 | 5/1990 | Loschiavo | 424/409 |
| 4,961,929 | 10/1990 | Gurvich et al. | 424/196.1 |
| 5,106,622 | 4/1992 | Sherwood et al. | 424/195.1 |
| 5,118,506 | 6/1992 | Eichoefer et al. | 424/196.1 |
| 5,320,066 | 6/1994 | Gunter | 119/28.5 |
| 5,449,517 | 9/1995 | Fitzjarrell | 424/195.1 |

OTHER PUBLICATIONS

Vapour Toxicity and Repellency of Some Essential Oils to Insect Pests, S. M. Ahmed et al, Indian Perfumer, 30 (1), 1986, pp. 273–278.

Killing Activities of the Volatiles Emitted from Essential Oils for Dermatophagoides pteronyssinus, Dermatophagoides farinae and Tyrophagus putrescentiae, Fujio Watanabe, et al, Shoyakugaku Zasshi 43 (2), pp. 163–168 (1989).

Behavior of *Tetranychus urticae* Toward Essential Oil Mixtures from Strawberry Foliage, J. G. Rodriguez et al, J. Chem. Ecol., 1976, vol. 2, No. 2, pp. 221–230.

Insect antifeedant action of some essential oils, Pesticides, Jul., 1981, pp. 21–22.

*Primary Examiner*—John W. Rollins
*Attorney, Agent, or Firm*—Arnold, White & Durkee

[57] ABSTRACT

The present invention provides a controlled-release insect repellent device and a method for repelling insects from food, tobacco, or other consumable items. The controlled-release insect repellent device comprises an insect repellent composition contacting a substrate. The controlled-release insect repellent device is prepared by a method comprising applying the insect repellent composition to the substrate wherein the repellent compound used is present in the controlled-release insect repellent device in an amount such that when it is released it is non-toxic to humans and animals. The method for repelling insects comprises placing the controlled-release insect repellent device in an area where insects may be present. The insect repellent composition comprises a repellent compound and a controlled-release agent, the controlled-release agent which comprises a compound which may be synthetic and/or natural, and, optionally, a solvent. The repellent compound may be chosen from the group consisting of essential oils and active ingredients of essential oils.

37 Claims, 4 Drawing Sheets

CONTROLLED-RELEASE INSECT REPELLENT DEVICE

FIELD OF THE INVENTION

The present invention relates to an insect repellent device having controlled release of an insect repellent compound and a method for repelling insects from food, tobacco, or other consumable items using the controlled release insect repellent device. The controlled-release insect repellent device is safe for contact with consumable items and may be used in any area from which it is desired to exclude insects. The controlled-release insect repellent device is also environmentally safe.

BACKGROUND OF THE INVENTION

Compounds which kill insects are known but are often unpleasant for humans to come in contact with. Many have been found to be toxic to humans and to the environment and cannot be placed in direct or indirect contact with food, tobacco, or other consumable items. Furthermore, FDA and EPA approval of new compounds for pest control may take years to obtain. The present invention provides a controlled-release insect repellent device containing compounds which are effective at repelling insects, pleasant for most who come into contact with them, and which do not adversely affect the environment. Many of the insect repellent compounds with which the controlled-release insect repellent device of the present invention may be used are already approved for food and medical usage.

SUMMARY OF THE INVENTION

The present invention provides an environmentally-friendly, controlled-release insect repellent device for repelling insects from food, tobacco, or other consumable items which is safe for use with food, including food for infants, and not harmful to humans, animals, or to the environment. The present invention also provides a method for repelling insects from food, tobacco, or other consumable items using the controlled-release insect repellent device. The controlled-release insect repellent device comprises an insect repellent composition contacting a substrate. The controlled-release insect repellent device is prepared by a method comprising applying the insect repellent composition to the substrate. The method for repelling insects comprises placing the controlled-release insect repellent device in an area where insects may be present. The insect repellent composition used in the controlled-release insect repellent device is prepared by mixing a repellent compound, a controlled-release agent and, optionally, a solvent to form a precursor composition which is then applied to a substrate and dried if necessary to form the insect repellent composition. Other additives such as coupling agents, agents to control the release rate, and thickeners may also be used. The repellent compound may be chosen from the group consisting of essential oils and active ingredients of essential oils. Essential oils are defined as any of a class of volatile oils obtained from plants and possessing the odor and other characteristic properties of the plant. The controlled-release agent comprises a compound which may be synthetic and/or natural.

The controlled-release insect repellent device is beneficial because it contains only a small amount of the active ingredient in an insect repellent composition, the active ingredient is safe for use with food, tobacco, or other consumable items, and the vapor of the active ingredient is pleasant to most who come into contact with it. Further, the controlled-release insect repellent device remains active for the desired period of time which may be variable—short to long. The active ingredient is present in the controlled-release insect repellent device in an amount such that when it is released from the device, it is non-toxic to humans and animals.

BRIEF DESCRIPTION OF THE FIGURES

The advantages of the present invention will become apparent upon reading the following detailed description and upon reference to the accompanying figures, in which.

DETAILED DESCRIPTION OF THE INVENTION

Figure 1:
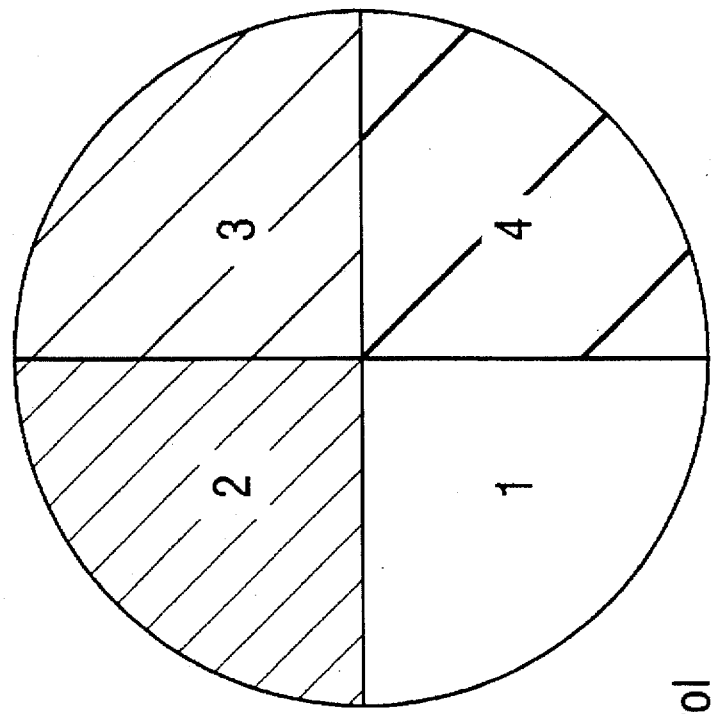
FIG. 1 shows the arena design used in a test of the efficacy of methyl salicylate as a repellent to the Indianmeal moth.

The environmentally-friendly, controlled-release insect repellent device of the present invention allows for controlled release of the insect repellent thus providing an insect repellent device which will remain useful for the desired period of time and which will be safer and healthier for use in products which adults, children and animals come into contact with. The device also provides insect repellence without an odor noticeable by humans.

The present invention teaches that the rate of release of the vapor of a compound having the ability to repel insects may be adjusted by the addition of a controlled-release agent. Mixing a repellent compound with a controlled-release agent in which the active ingredient in the repellent compound is miscible allows control of the release of the vapor of the active ingredient in some cases because of the affinity of the controlled-release agent for the active ingredient. Altering the relative ratios of the repellent compound and the controlled-release agent in the insect repellent composition and choosing the type, mount, and concentration of active (e.g., essential oil) and inactive (e.g., controlled-release agent) will allow for more particularized control of the release rate. In addition, mixing additives with the repellent compound will also contribute to the control. The ability to control the release rate is a benefit of the controlled-release insect repellent device. Controlling the release rate extends the duration of the effectiveness of the insect repellent device thereby lengthening its useful life. Controlling the release rate also prevents excess exposure of the repellent compound to items in contact with or in the vicinity of the device.

The controlled-release insect repellent device has a further advantage in that it may be used to repel insect from food, tobacco, or other consumable items and may be used in either direct or indirect contact with consumable items. In addition, the device may also be used with non-consumable items, i.e., textiles and fur. The repellent compound is present in an mount such that when it is released, it is non-toxic to adults, children and animals. Control of the release rate of the repellent compound where the controlled-release insect repellent device is in contact with consumable items will allow the repulsion of insects without releasing undue odors or changing the taste of the consumable items—problems which are undesirable in consumer products.

The insect repellent composition of the present invention is prepared by mixing a repellent compound with a controlled-release agent and, optionally, a solvent, and/or other additives to form a precursor mixture and then applying the precursor mixture to a substrate. The precursor mixture is then dried if necessary to form the insect repellent composition on the substrate. The pH of the precursor mixture which may be used is limited only by the effect upon the substrate and coating material. Preferably, the precursor mixture is dried after application to the substrate. The temperature of drying is not believed to be important, but the temperature ranges which may be used are in the range of from about −17° C. to about 315° C., preferably about 37° C. to about 205° C., most preferably about 37° C. to about 150° C.

Examples of repellent compounds are essential oils such as almond bitter oil, anise oil, basil oil, bay oil, caraway oil, cardamon oil, cedar leaf oil, celery oil, chamomile oil, cinnamon leaf oil, citronella oil, clove oil, coriander oil, cumin oil, dill oil, eucalyptus oil, fennel oil, ginger oil, grapefruit oil, lemon oil, lime oil, mint oil, parsley oil, pepper oil, rose oil, spearmint oil (menthol), sweet orange oil, thyme oil, tumeric oil, and oil of wintergreen (also known as Gaultheria oil). Examples of the active ingredients in essential oils are citronellal, methyl salicylate, ethyl salicylate, propyl salicylate, citronellol, safrole, and D-limonene. The preferred repellent compound is the essential oil: oil of wintergreen or its active ingredient methyl salicylate.

The concentration of the repellent compound in the insect repellent composition after the insect repellent composition has been applied and dried on the substrate will range from about 0.1 wt. % to about 80 wt. %, preferably about 0.1 wt. % to about 40 wt. %, most preferably from about 0.1 wt. % to about 20 wt. %, (dry weight) with the balance of the insect repellent composition being the amounts of the controlled-release agent, solvent, and/or other additives which have not evaporated during the drying step.

The controlled-release agent comprises a compound which will control the rate of release of the repellent compound from the device. Any compound which is approved for use in either direct or indirect contact with food, tobacco, or other consumable items may be used as the controlled-release agent. Examples of the controlled release agent are polymers, both inorganic and organic, including natural, synthetic, and semi-synthetic organic polymers. Examples of these polymers are latex resins (e.g., styrenated acrylic resins and styrenated butadiene resins), solution acrylics, polyvinyl resins, sodium alginates, natural gums or hydrocolloids (e.g., gum arabic, sodium alginates, guar, and pectin), synthetic gums (e.g., fumeric modified resins), polyethylene waxes, wax emulsions, polymeric printing inks (e.g., special formulations such as U.V. and electron beam), polymeric aqueous foams, adhesives (e.g. cold set type, hot melt, printable heat sets and ultrasonic types, and laminating adhesives of reactive and non-reactive types;), polymeric protective coatings, primers and miscellaneous natural resin formulations (e.g., copal, zien, and protein). Examples of non-polymeric controlled-release agents which may be used are non-polymeric printing inks, non-polymeric aqueous foams, non-polymeric protective coatings, and fillers such as sawdust, clay and zolites. Other compounds not listed which allow control of the release rate of the repellent compound from the device are also contemplated.

The controlled-release agent may also optionally comprise a solvent and/or additives such as coupling agents or dispersants (e.g., 2-amino-2-methyl-1-propanol). The solvents which may be used are compatible with the repellent compound and the controlled-release agents being used to form the precursor mixture. Examples of solvents are water, alcohols, acetone, ammonia, ether, and glacial acetic acid. Where the compound used in the controlled-release agent is in a liquid or molten state, there may be no need for a solvent in the controlled-release agent.

The controlled-release agent should not detrimentally affect the properties of the substrate (e.g., by discoloring or changing the shape or strength of the substrate) or interfere with the processing of the substrate (e.g., by interfering with further coating of the substrate after application of the insect repellent composition).

The amount of the insect repellent compound present in the precursor mixture before application to the substrate to form the insect repellent composition ranges from about 0.05% to about 40%, preferably from about 0.05 to about 20%, most preferably from about 0.05 to about 10% (wet weight). The amount of insect repellent present in the insect repellent composition after application to the substrate and optional drying ranges from about 0.1% to about 80%, preferably from about 0.1% to about 40%, most preferably from about 0.1% to about 20% (dry weight). All percentages are percent by weight.

Examples of substrates upon which the precursor mixture may be applied are materials such as paper, paperboard, corrugated boxes as well as their individual components of liners or medium, plastic, plastic sheeting, cloth, metals such as aluminum, and metallized films which may have additional layers or coatings on them. Preferably, the substrate is in the form of a container which holds comestible materials for adults, children and animals. Examples of containers are folding cartons, corrugated boxes, fluted cartons and boxes, sacks, bags, molded fibers, pressed trays, flexible packages, plastic and aluminum packages and wrappings. The substrate may also in the form of an object which is to be placed in an area from which insects are to be repelled, e.g., a piece of paper, paperboard, plastic or metal which is placed in a food storage area, a cupboard, or a building.

Examples of methods by which the controlled-release insect repellent device may be coated with the precursor mixture are spray nozzle, rod coater, blade coater, air knife coater, roll coater, multiple roll transfer, controlled and uncontrolled drip, wet bath dip, curtain coater, and vacuum and non-vacuum impregnation. Where the controlled-release insect repellent device is a package, printing may be also be applied to the package. Printing methods which may be used with the invention formulation are gravure, flexographic, screen, letterpress, web offset, sheetfed offset, and ink jet.

The rate of release of the active ingredient vapor from the insect repellent composition may also be controlled by applying a directional barrier to the controlled-release insect repellent device. Such a barrier may also control the direction in which the vapor is released. The barrier material may be a part of the substrate or may be applied directly on top of the controlled-release insect repellent device. The barrier material may be made out of a foil for a complete barrier or made out of materials such as film including multilayered films, paper, coated substrates, or even applied liquid coatings of a solvent, solventless or aqueous nature for a less than complete barrier. Further examples of barriers are aluminum foil, paper, polymeric film, or layered structures thereof. Examples of polymeric films are polyethylene, polyester, polypropylene, polyvinyl alcohol, ethylvinyl alcohol, polyvinyl chloride, polyvinylidene chloride, polyvinyl acetate, and layered structures thereof. Specific barriers which have been tested are aluminum foil, polyethylene, polyester film, polypropylene film, and paper. The paper tested was coated with both aqueous and non-aqueous solvent barrier coatings.

Examples of insects for which the composition may be used are insects such as mites, (e.g., the European dust mite, *Dermatophagoides pteronyssinus*, American house dust mite, *Dermatophagoides farinae* and the mold mite, *Tyrophagus putrescentiae*), moths and moth larvae (such as from the Indianmeal moth, *Plodia interpunctella* (order:family=*lepidoptera:pyralidae*)), weevils (e.g., the rice weevil, *Sitophilus oryzae*), beetles (e.g., the pulse beetle, *Callosobruchus chinensis*. and the spice beetle, *Stegobium paniceum*), and the house fly (*Musca domestica*).

The controlled-release insect repellent device of the present invention is intended for use in repelling insects from food, tobacco, or other consumable items. The controlled-release insect repellent device may be in direct contact with food or other consumables (e.g., a box for storing infant cereal) or in the vicinity of food (indirect contact, e.g., in a cupboard).

EXAMPLE 1

An experiment was done to test the efficacy of methyl salicylate as a repellent to the Indianmeal moth in the controlled-release insect repellent device of the present invention. The objectives of this study were to evaluate pure (reagent grade) methyl salicylate as a repellent; evaluate pH stabilized (reagent grade) methyl salicylate as a repellent; and evaluate two mixtures of the uncured (undried) controlled-release agent—45% solids (high solids, "H/S") and 10% solids (low solids, "L/S")—with two rates of methyl salicylate—(0.1 and 0.2 v/v) as a repellent.

Methods and Materials

The efficacy studies were carded out in plastic petri dish arenas (radius=10 cm, height=2.54 cm) fired with plastic lids (FIG. 1). The lids were equipped with flow-through ventilation, and demarcated into four quadrants with a felt marker. The quadrants were numbered from 1 to 4, and the treatment was always placed into the outside center of number 1.

A Whatman No. 1 filter paper, fitting the inside diameter of the arena, was used as an underlying substrate. A 2.54× 0.5×0.05 cm Whatman No. 1 filter paper was folded into a z shape and put in the middle of quadrant Number 1 to be used as a treatment platform. This platform raised the treatment dosage approximately 1.5 cm off the substrate and facilitated evaporation without direct tactile contact with insects.

At the start of each experiment, one of eight treatments (replicated 3–5 times) of 0.5 mL each was pipetted onto the platform as follows: 0.1 methyl salicylate (reagent grade) in ethyl alcohol (70%) (positive control), 70% ethyl alcohol (solvent control), pH stabilized 0.1 and 0.2 methyl salicylate in H/S and L/S polymer mixtures (=4 treatments), or the H/S:L/S (v/v) mixture (polymer control).

Before the treatments were placed into the arenas, 20 Indianmeal moth adults were aspirated from rearing jars, anaesthetized with $CO_2$, and carefully placed into the chamber. The insects were allowed to acclimate for at least 5 minutes at approximately 25.6° C. (78° F.).

After the treatment was pipetted onto the platform, the number of Indianmeal moths in the treatment quadrant versus each of the other 3 arena quadrants was determined at time intervals of 1, 5, 10 and 15 minutes. If the treatment was a repellent, more moths would be found in quadrants 2, 3 and 4 on average.

All data were plotted, then submitted to standard statistical summarization before paired T tests and/or analysis of variance with mean separations were performed.

A "no effect" response should find the same number of moths in each quadrant on average. If repellency exists, significant fewer moths will be found in the number 1 quadrant where the treatment resides than the other quadrants.

Figure 2:
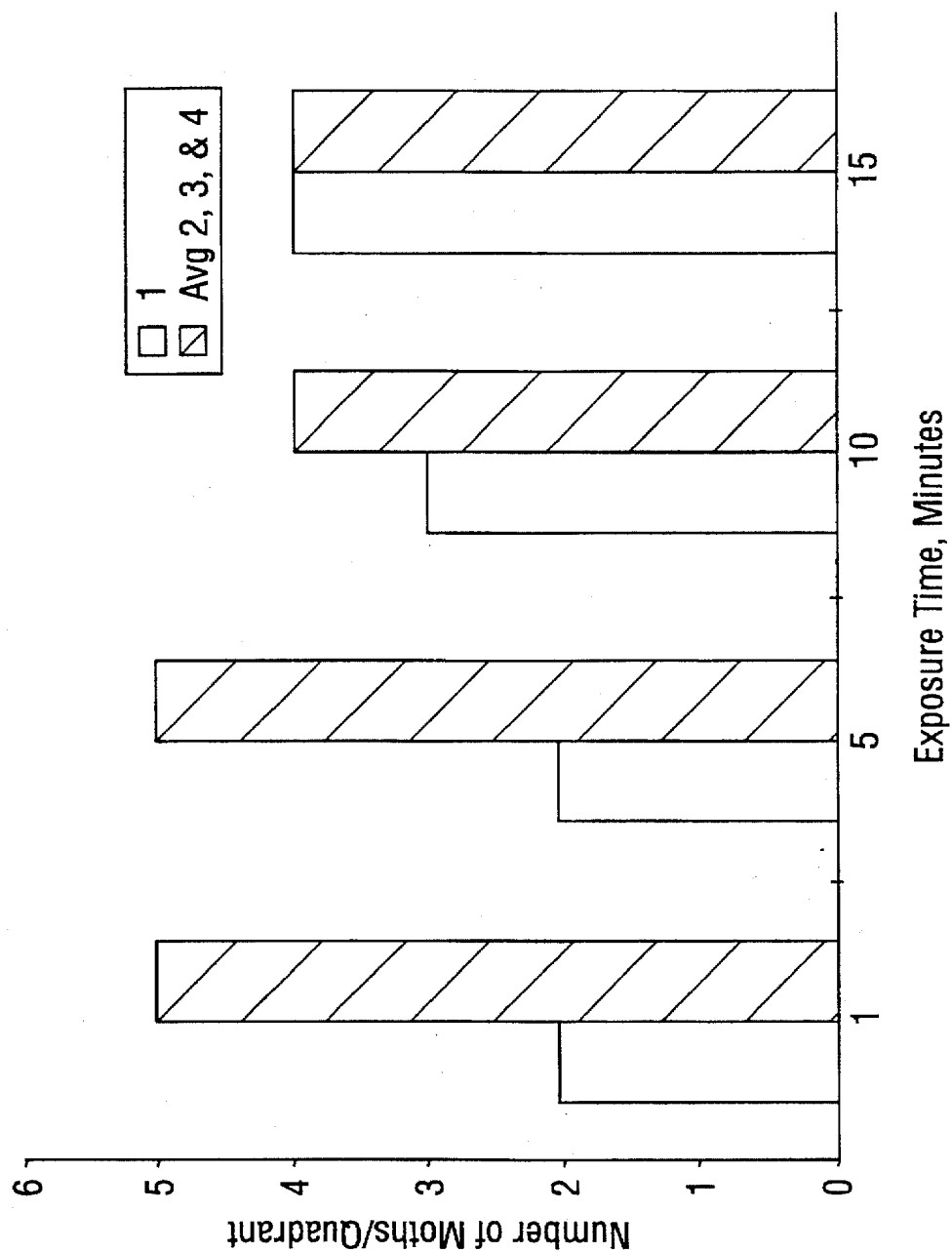
FIG. 2 shows the response of the Indianmeal moth to methyl salicylate.

A typical example for all eases that contained methyl salicylate is shown in FIG. 2 and presented in Table 1.

TABLE 1

Moth Response to the Controlled-release insect repellent device

| | | Exposure Time (min) | | | |
|---|---|---|---|---|---|
| | Position | 1 | 5 | 10 | 15 |
| | | Number of Moths | | | |
| | 1 | 2 | 2 | 3 | 4 |
| | Avg 2, 3, & 4 | 5 | 5 | 4 | 4 |
| Mortality % | Treated | 0 | 0 | 26 | 35 |
| | Control | 0 | 0 | 0 | 0 |

Table 1 shows that after one minute, the average number of moths found in the treatment quadrant was 2 compared with 5 in quadrants 2, 3, and 4. Note that the control moth distribution between the four quadrants averaged 4.7±0.62 and was not different between control quadrants, but was significantly different ($p \leq 0.05$) from the treatment quadrant. This indicates a strong repellence.

After 5 minutes the repellency remained strong with an average of 2 adult moths in the treatment quadrant versus 5 in the other quadrants.

From 10 minutes until the end of the test at 15 minutes the adult moths were habituated, anaesthetized or dead. Apparently the dosage was too high to prevent receptor attenuation and/or caused mortality.

Figure 3:
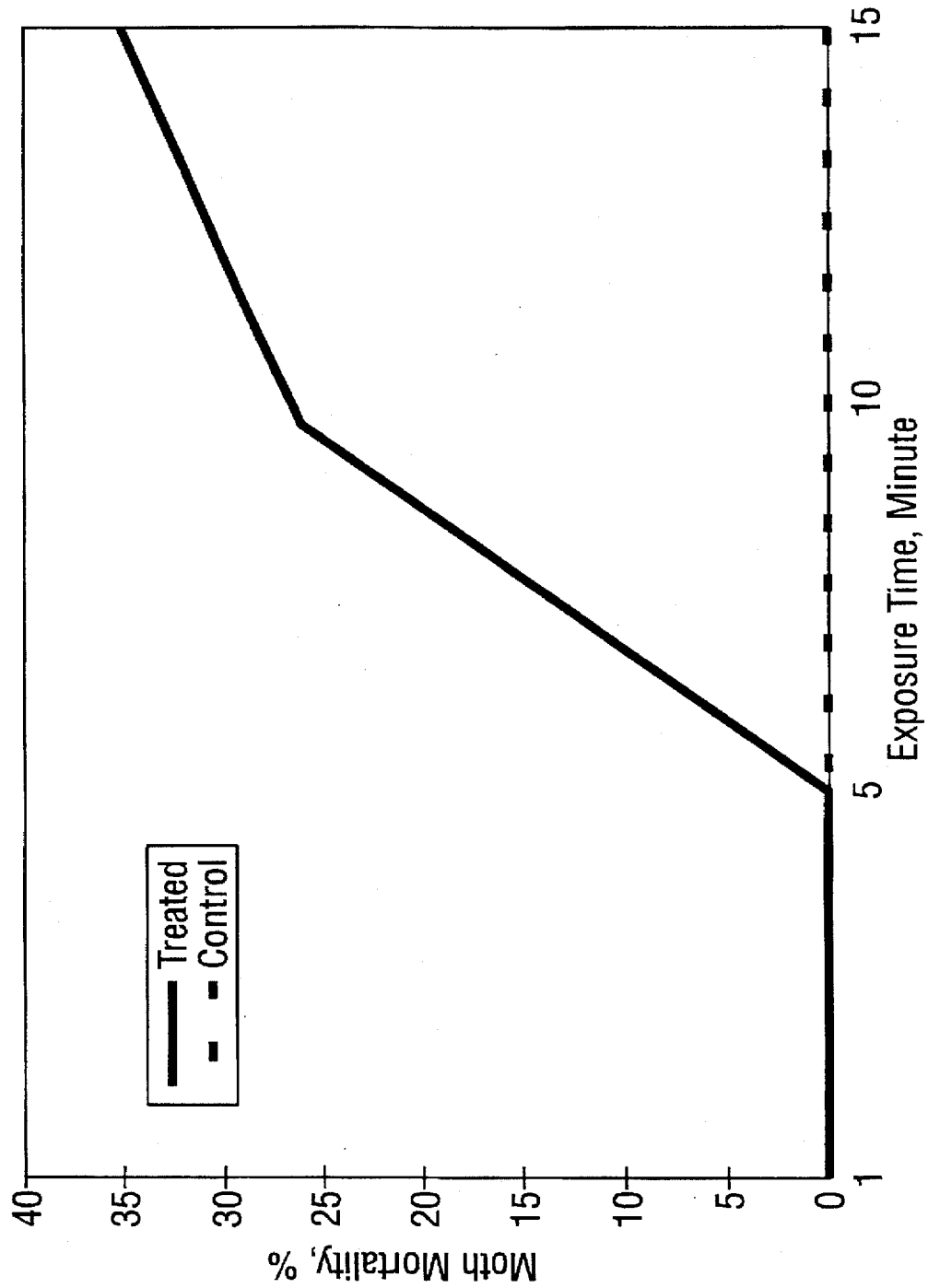
FIG. 3 shows the effect on the Indianmeal moth of exposure to an inventive controlled-release insect repellent device containing methyl salicylate.

Table 1 and FIG. 3 reflect a typical average percent mortality for all cases that contained methyl salicylate in either ethyl alcohol or controlled-release agent. This treatment elicited moribund moths in 10 minutes and progressively more mortality with exposure time. After 15 minutes mortality averaged 35%.

Discussion and Conclusions

Methyl salicylate is a potent repellent of Indianmeal moth adults. In every experiment and in each replicate within an experiment this was abundantly clear. At the high dosage (0.2 v/v), methyl salicylate elicited hyperactivity, wing fluttering, avoidance behavior and eventual death. At the half rate (0.1 v/v) treatment mixtures these symptoms were delayed in time and intensity, but occurred in every treatment replicate.

Both the reagent grade and pH stabilized methyl salicylate formulations cause more mortality than the polymer formulations. They also habituated the moths at shorter times than the other formulations. This means that the polymers were slowing the release of methyl salicylate into the atmosphere. Thus, the polymer will extend the repellent life of methyl salicylate.

No deterrence or mortality was observed in any of the controls. That is to say that neither ethyl alcohol as a solvent for reagent grade methyl salicylate or the mixture of H/S and L/S controlled-release agent alone cause mortality. Yet all the rates and controlled-release agent mixtures of methyl salicylate caused mortality.

EXAMPLE 2

An experiment was done to determine the impact of the insect repellent composition of the present invention on the invasion of packaged infant cereal (banana rice) by the Indianmeal moth. Adult moths attracted to food packages and will oviposition (lay) their eggs on them. The eggs hatch, producing larvae which then bore into the packages, leaving holes which allow exposure of the food to the environment. After feeding on the food, the larvae grow, by shedding their skin—usually 4–5 times, spin silk, go through the pupae stage, and develop into adult moths. The moth larvae will grow inside the food package to pupae and then to adult moths measuring as much as 1.25 cm (½ inch).

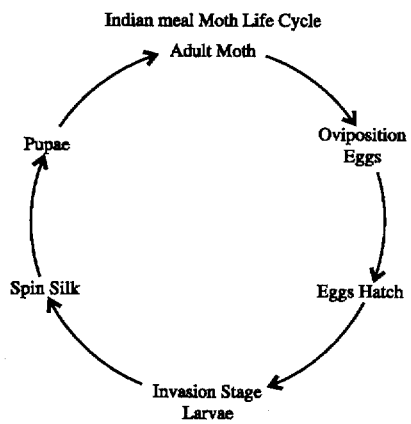

Indian meal Moth Life Cycle

Preparation of Insect Repellent Composition

Precursor insect repellent compositions were prepared by mixing a controlled-release agent with a repellent compound. In some compositions, other additives were also used.

Composition A was prepared by mixing the controlled-release agent with additives in the following proportions: 80 wt. % styrenated acrylic resin (controlled-release agent), 10 wt. % non-ionic poly wax (coupling agent), and 10 wt. % of a 2% aqueous solution of sodium alginate (thickener). The sodium alginate solution had a viscosity of 20 seconds, #3 Zahn cup (i.e., 44 mL took 20 seconds to flow through an orifice in the bottom of a metal cup having a diameter of 0.38 cm (0.148 in); measured using a Zahn viscosimeter). Next, the controlled-release agent mixture was added to a repellent compound (methyl salicylate) and a solvent (deionized water) to form Composition A.

Composition B was prepared by mixing the controlled-release agent directly with the repellent compound. The controlled-release agent was a commercially available primer and the repellent compound was methyl salicylate.

Compositions A and B were prepared with three different concentrations of the repellent compound. The compositions all contained 90% controlled-release agent mixture and either 0.5%, 2.5%, or 5.0% repellent compound (wet weight) with the balance being the solvent. The viscosity of the compositions before the addition of the solvent was measured as 18–20 seconds, #2 Zahn cup (i.e., 44 mL took 18–20 seconds to flow through an orifice having a diameter of 0.27 cm (0.108 in)). The pH of the final compositions was between about 9 and about 9.5.

Treatment of Paperboard

Figure 4:
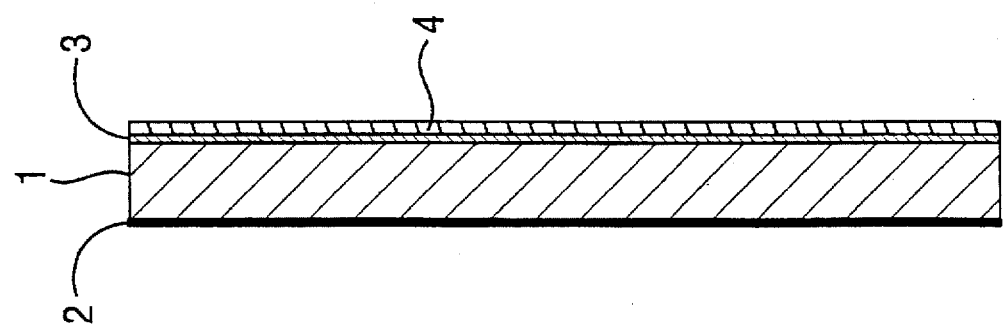
FIG. 4 shows an example of a controlled-release insect repellent device of the present invention.
Figure 5:
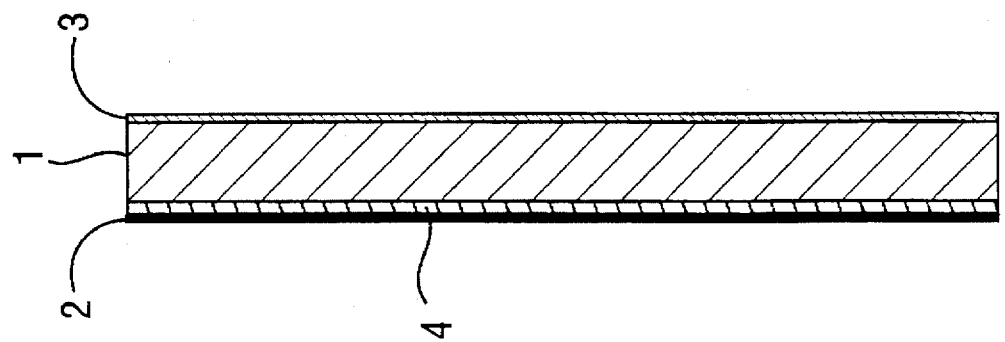
FIG. 5 shows an example of a controlled release insect repellent device of the present invention.

The precursor insect repellent compositions A and B were applied to paperboard by two Method A and Method B, respectively, to produce insect repellent compositions on a substrate having three different dry weight concentrations [1%, 5%, and 10% dry weight of a 0.976 kg coating/$m^2$ paperboard surface (0.2 lbs/1000 $ft^2$)]. As shown in FIGS. 4 and 5, the substrate consisted of paperboard 1 coated with an inner coating of polyethylene 2 and an outer clay coating 3. The insect repellent composition 4 was applied to this substrate in either of two locations. FIG. 4 shows the result of Method A, wherein the insect repellent composition 4 was applied over the outer clay coating 3 of the carton at approximately the same time as the polyethylene coating 2 was being extruded to the inner side of the paperboard. FIG. 5 shows the result of Method B, wherein the insect repellent composition 4 was applied to the backside of the paperboard prior to the extrusion of polyethylene 2 over the backside of the paperboard (i.e., polyethylene was extruded over the insect repellent composition). Afterwards, the paperboard was converted to cartons of the type commercially used for cereal which have a polyethylene coating coveting the backside of the paperboard and a clay coating on the outside of the cereal box.

The insect repellent-treated cartons were then filled with banana rice baby cereal and sealed closed with glue.

Indianmeal Moth Invasion Testing

More than six weeks after the paperboard was treated with the insect repellent composition, the cartons were exposed to the Indianmeal moth in test chambers. The treated cartons were divided into 8 groups (2 control (untreated) groups, 3 groups treated with the insect repellent composition by Method A, and 3 groups treated by Method B). One of the control groups was tested in isolation in a separate chamber while the other was placed among the treated groups.

The difference between the 3 treated groups for both of Methods A and B is in the methyl salicylate content in the dried coating of 1, 5 and 10%.

The total duration of the invasion testing was 8 weeks. From the start of the testing and at the beginning of each subsequent week, fresh mature moth adults were introduced to the test chambers. At the start of the testing these moths were capable of producing larvae (the invasion stage of the moth) at a calculated ratio of 156/carton.

The cartons which were placed randomly in the test chambers were sampled by pulling 6 cartons of each group at 0, 1, 2, 4, 6 and 8 weeks. The total number of cartons used was 288 cartons, of which 48 were not exposed to the insect repellent composition and the total number of larvae was about 37,500.

For each addition of new moths, this total larvae was not changed while due to sample pulling, the number of cartons in the test chambers declined. Thus, at the last week of testing, the ratio of larvae to carton which was increasing incrementally with each pull, was increased from 156 to 1,250. Furthermore, cartons that remained to the full 8 weeks of testing were exposed to a total of 5,600 larvae/carton during the duration of the testing.

The spacing between the cartons was about 1.3 cm (0.5 inches) during the first week of testing, increasing gradually with each sample pull to about 15.2 cm (6.0 inches) at the end of the test due to removal of cartons for sampling. The conditions in the test chambers were controlled to simulate the conditions in a house cupboard; the temperature was maintained at approximately 25±1.9° C. (77±3.5° F.) and the air was completely replaced 12 times per day.

The invasion of the cartons by moth larvae was noted as a percent of cartons infested by a moth at any of the moth growth development stages, the number of larvae per carton, and whether the growth development of the larvae was normal at 0, 1, 2, 4, 6, and 8 weeks after exposure to the moth. Cartons were incubated individually in sealed plastic bags for an additional two weeks to allow larvae to grow so that they would be large enough to be counted. The results appear in the following table.

week. Furthermore, the cartons treated with the insect repellent composition containing the highest concentration of the repellent compound (10%) contained only stunted larvae after the 8th week when treated using Method B, and contained no larvae at all when treated using Method A.

The success of the insect repellent composition in preventing the infestation of the cartons is impressive in view of a number of factors. The cumulative intensity of larvae (5,600 per carton; 156 per carton at the start of the test up to 1,250 per carton at the 8th week of the test) was much higher than a packaged food carton would likely be exposed to in a normal household. In addition, over four months had elapsed from the application of the insect repellent composition to the cartons and the completion of the experiment. Finally, it was observed that when the moths were first introduced into the test chamber, they tried to escape rather

TABLE 2

|  | Infestation (%) | Number of larvae per carton | Normal Growth Development | Infestation (%) | Number of moths per carton | Normal Growth Development | Infestation (%) | Number of larvae per carton | Normal Growth Development |
|---|---|---|---|---|---|---|---|---|---|
| Time (weeks) | | 0 | | | 1 | | | 2 | |
| Control | | | | | | | | | |
| - isolated | 0 | 0 | — | 33 | 2-5 | Yes | 67 | 2-5 | Yes |
| - not isolated | 0 | 0 | — | 17 | 1 | No | 0 | 0 | — |
| Method A 1% | 0 | 0 | — | 0 | 0 | — | 17 | 1 | No |
| 5% | 0 | 0 | — | 0 | 0 | — | 0 | 0 | — |
| 10% | 0 | 0 | — | 0 | 0 | — | 0 | 0 | — |
| Method B 1% | 0 | 0 | — | 0 | 0 | — | 0 | 0 | — |
| 5% | 0 | 0 | — | 0 | 0 | — | 0 | 0 | — |
| 10% | 0 | 0 | — | 0 | 0 | — | 0 | 0 | — |
| Time (weeks) | | 4 | | | 6 | | | 8 | |
| Control | | | | | | | | | |
| - isolated | 83 | 6-10 | Yes | 100 | >15 | Yes | 100 | >15 | Yes |
| - not isolated | 17 | 1 | No | 17 | 1 | Yes | 83 | 1 | Yes |
| Method A 1% | 0 | 0 | — | 0 | 0 | — | 50 | 2-5 | Yes |
| 5% | 0 | 0 | — | 17 | 1 | No | 50 | 1 | Yes |
| 10% | 0 | 0 | — | 0 | 0 | — | 0 | 0 | — |
| Method B 1% | 0 | 0 | — | 0 | 0 | — | 50 | 1 | Yes |
| 5% | 0 | 0 | — | 0 | 0 | — | 33 | 1 | Yes |
| 10% | 0 | 0 | — | 0 | 0 | — | 17 | 1 | No |

The results presented in Table 2 show that none of the cartons were infested during packaging and transportation as evidenced by the lack of infestation at the initiation of the test which occurred approximately two months after treatment with the insect repellent composition.

The isolated control cartons were infested at a level of 33% after the first week by 2-5 normally-developed moth larvae per carton. After the 2nd week, the percentage doubled to 67%, and rose to 100% infestation by over 15 normally-developed moths per carton after the 6th week.

The non-isolated control cartons which were placed and tested in the vicinity of treated cartons showed 17% infestation by only one stunted moth larva after the 1st and 4th weeks but none after the 2nd week. After the 6th week, the cartons were infested at a level of 17% by one normally-developing moth larva. By the 8th week, 83% of the cartons were infested by 1 normally-developed moth per carton. The slower infestation of the control cartons placed in the vicinity of the treated cartons indicates that the treated cartons afforded some secondary protection to the control cartons.

The treated cartons were infested with a single stunted larva after the 2nd and 6th weeks, but none were infested with normally developing moth larvae until after the 8th than to seek out the food-containing cartons. Thus, it is likely that the infestation of the treated cartons would have been reduced, perhaps significantly, if the cartons had been tested soon after the application of the insect repellent composition, the cumulative intensity of larvae had been at a normal range, moths had not been forced to stay in the vicinity of the cartons.

We claim:

1. A controlled-release insect repellent device for repelling insects from food, tobacco, or other consumable items, comprising an insect repellent composition contacting a substrate;

wherein the insect repellent composition comprises (a) a repellent compound chosen from the group consisting of essential oils accepted for food and medical use and active ingredients of said essential oils, (b) a controlled-release agent, and optionally, (c) a solvent;

wherein the repellent compound used in the controlled-release insect repellent device is present in an amount such that it is non-toxic to humans and animals, and wherein the controlled-release agent will control the rate of release of the repellent compound from the device such that its odor is not objectionable or noticeable by humans.

2. The controlled-release insect repellent device of claim 1 wherein the repellent compound is an essential oil.

3. The controlled-release insect repellent device of claim 1 wherein the repellent compound is present in the insect repellent composition before application to the substrate in an amount in the range of from about 0.05 to about 40% by weight.

4. The controlled-release insect repellent device of claim 3 wherein the repellent compound is present in the insect repellent composition before application to the substrate in an amount in the range of from about 0.05 to about 20% by weight.

5. The controlled-release insect repellent device of claim 1 wherein the repellent compound is present in the insect repellent composition before application to the substrate in an amount in the range of from about 0.05 to about 10% by weight.

6. The controlled-release insect repellent device of claim 1 wherein the repellent compound is present in the insect repellent composition after application to the substrate and drying in an amount in the range of from about 0.1% to about 80% by weight.

7. The controlled-release insect repellent device of claim 6 wherein the repellent compound is present in the insect repellent composition after application to the substrate and drying in an amount in the range of from about 0.1% to about 40% by weight.

8. The controlled-release insect repellent device of claim 7 wherein the repellent compound is present in the insect repellent composition after application to the substrate and drying in an amount in the range of from about 0.1% to about 20% by weight.

9. The controlled-release insect repellent device of claim 1 wherein the repellent compound is chosen from the group consisting of almond bitter oil, anise oil, basil oil, bay oil, caraway oil, cardamon oil, cedar leaf oil, celery oil, chamomile oil, cinnamon leaf oil, citronella oil, clove oil, coriander oil, cumin oil, dill oil, eucalyptus oil, fennel oil, ginger oil, grapefruit oil, lemon oil, lime oil, mint oil, parsley oil, pepper oil, rose oil, spearmint oil, sweet orange oil, thyme oil, turmeric oil, oil of wintergreen, citronellal, methyl salicylate, ethyl salicylate, propyl salicylate, citronellol, safrole, and D-limonene.

10. The controlled-release insect repellent device of claim 9 wherein the repellent compound is an active ingredient in an essential oil.

11. The controlled-release insect repellent device of claim 10 wherein the repellent compound is oil of wintergreen.

12. The controlled-release insect repellent device of claim 9 wherein the repellent compound is methyl salicylate.

13. The controlled-release insect repellent device of claim 1 wherein the substrate is chosen from the group consisting of paper, paperboard, corrugated boxes, liners of corrugated boxes, medium of corrugated boxes, plastic, plastic sheeting, cloth and metals.

14. The controlled-release insect repellent device of claim 13 wherein the substrate is paperboard.

15. The controlled-release insect repellent device of claim 13 wherein the substrate is in the form of a container.

16. The controlled-release insect repellent device of claim 15 wherein the container contains food.

17. The controlled-release insect repellent device of claim 15 wherein the container contains tobacco.

18. The controlled-release insect repellent device of claim 1 wherein the controlled-release agent is chosen from the group consisting of polymers, non-polymeric printing inks, non-polymeric aqueous foams, non-polymeric protective coatings, and fillers.

19. The controlled-release insect repellent device of claim 18 wherein the controlled-release agent is chosen from the group consisting of latex resins, solution acrylics, polyvinyl resins, natural gums, synthetic gums, polyethylene waxes, wax emulsions, polymeric printing inks, polymeric aqueous foams, adhesives, polymeric protective coatings, primers and natural resin formulations.

20. The controlled-release insect repellent device of claim 19 wherein the controlled-release agent is a latex resin.

21. The controlled-release insect repellent device of claim 20 wherein the controlled-release agent comprises a styrenated acrylic resin.

22. The controlled-release insect repellent device of claim 20 wherein the controlled-release agent comprises a styrenated butadiene resin.

23. The controlled-release insect repellent device of claim 19 wherein the controlled-release agent comprises a natural or synthetic gum.

24. The controlled-release insect repellent device of claim 23 wherein the controlled-release agent comprises gum arabic.

25. The controlled-release insect repellent device of claim 19 wherein the controlled-release agent comprises a polyethylene wax or wax emulsion.

26. The controlled-release insect repellent device of claim 1 wherein the controlled-release agent comprises an adhesive.

27. The controlled-release insect repellent device of claim 26 wherein the controlled-release agent comprises a laminating adhesive.

28. The controlled-release insect repellent device of claim 19 wherein the controlled-release agent comprises a primer.

29. The controlled-release insect repellent device of claim 19 wherein the controlled-release agent comprises a sodium alginate.

30. The controlled-release insect repellent device of claim 23 wherein the controlled-release agent comprises a fumeric modified resin.

31. The controlled-release insect repellent device of claim 19 wherein the controlled-release agent is copal, zien, or protein.

32. The controlled-release insect repellent device of claim 1 wherein the controlled-release agent comprises a styrenated acrylic resin, the repellent compound comprises methyl salicylate, the solvent is water, and the insect repellent composition further comprises a non-ionic polyethylene wax.

33. The controlled-release insect repellent device of claim 1 wherein the solvent is water.

34. The controlled-release insect repellent device of claim 1 further comprising a directional barrier in contact with the substrate to control the direction from which vapor from the repellent compound is released.

35. The controlled-release insect repellent device of claim 34 wherein the directional barrier comprises aluminum foil, paper, a polymeric film, or layered structures thereof.

36. The controlled-release insect repellent device of claim 35 wherein the directional barrier comprises a polymeric film chosen from the group consisting of polyethylene, polyester, polypropylene, polyvinyl alchol, ethylvinyl alcohol, or layered structures thereof.

37. A method for repelling insects from food, tobacco, or other consumable items comprising placing the controlled-release insect repellent device of claim 1 in the vicinity of food, tobacco, or other consumable items.

* * * * *